United States Patent [19]

Johnson et al.

[11] 4,020,069

[45] Apr. 26, 1977

[54] PREPARATION OF AROMATIC TETRACARBOXYLIC ACIDS

[75] Inventors: Donald S. Johnson, Scotia; Howard M. Relles, Rexford, both of N.Y.

[73] Assignee: General Electric Company, Schenectady, N.Y.

[22] Filed: July 25, 1975

[21] Appl. No.: 598,950

[52] U.S. Cl. .................. 260/520 E; 260/30.4 R; 260/78 TF; 260/326 A; 260/326 N; 260/326 S; 260/346.3; 260/516; 260/546
[51] Int. Cl.$^2$ .......................................... C07C 65/14
[58] Field of Search ........ 260/516, 517, 520, 520 E

[56] References Cited
UNITED STATES PATENTS 3,879,428   4/1975   Heath et al. ..................... 260/516

OTHER PUBLICATIONS

*Dimethyl Sulfoxide as a Reaction Solvent*, Crown Zellerbach, Chemical Products Division, Camas, Washington (1968), pp. 2, 7–15.
Soine et al, *Inorganic Pharm. Chem.*, 7th edition, Lea & Febiger, Philadelphia, Pa. pp. 288–289 (1961).

*Primary Examiner*—James O. Thomas, Jr.
*Assistant Examiner*—G. T. Breitenstein
*Attorney, Agent, or Firm*—Joseph T. Cohen; Jerome C. Squillaro

[57] ABSTRACT

Aromatic tetracarboxylic acids can be prepared by effecting reaction between a 4-nitro-N-alkylphthalimide with an aromatic dihydroxy compound in the presence of potassium carbonate as a catalyst and using dimethyl sulfoxide as a solvent.

1 Claim, No Drawings

PREPARATION OF AROMATIC TETRACARBOXYLIC ACIDS

This invention relates to the preparation of aromatic tetracarboxylic acids by the process of effecting reaction between a 4-nitro-N-alkylphthalimide with an aromatic dihydroxy compound in the presence of potassium carbonate as a catalyst and using dimethyl sulfoxide as a solvent.

More particularly, the invention is concerned with a process for making tetracarboxylic acids of the general formula

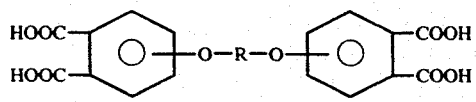
I which process comprises effecting reaction between a 4-nitro-N-alkylphthalimide of the general formula

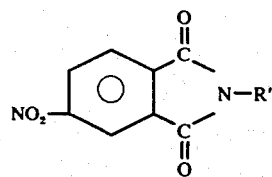
II with an aromatic dihydroxy compound of the general formula

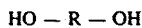 III where R is a member selected from the class consisting of (a) divalent radicals of the formula

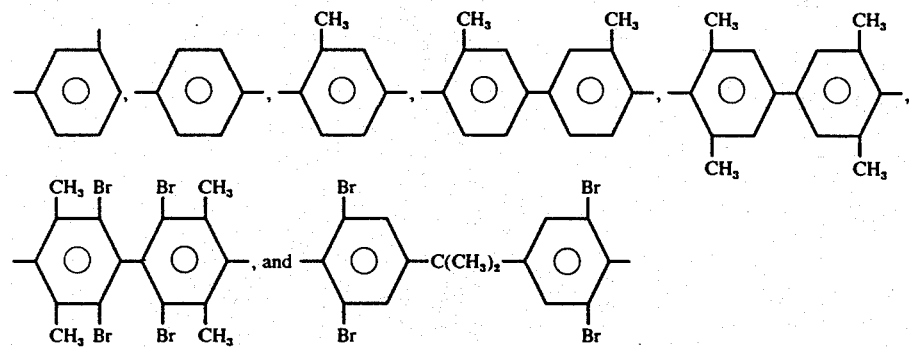

and (b) divalent organic radicals of the general formula

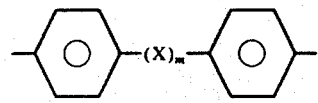

where X is a member selected from the class consisting of divalent radicals of the formulas $-C_yH_{2y}$,

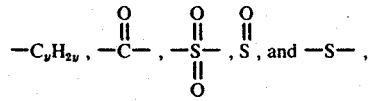

and $-S-$, where $m$ is 0 or 1, $y$ is a whole number from 1 to 5, and R' is an alkyl radical of from 1 to 2 carbon atoms, the said reaction being conducted in a solvent of dimethyl sulfoxide and in the presence of potassium carbonate.

Dianhydrides of the general formula

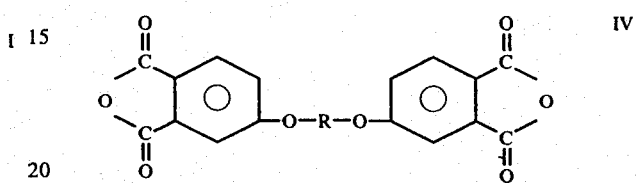
IV where R has the meanings given above have been used in the preparation of polymeric compositions by reacting the aforesaid dianhydrides with various organic diamines in the manner described in U.S. Pat. No. 3,847,867, issued Nov. 12, 1974, and assigned to the same assignee as the present invention which patent by reference is made part of the disclosures and teachings of the instant application. One of the important objectives in making these resins is to insure that the reactants required for such polymeric compositions are made as economically as possible in order that the ultimate cost of the resinous compositions will also be the lowest possible cost.

Several methods have been employed in the past for making the aforesaid tetracarboxylic acids including the process involving the hydrolysis of the corresponding tetracyano derivative as described in U.S. Pat. No. 3,787,475, issued Jan. 22, 1974, and assigned to the same assignee as the present invention. However, this process as well as other previous processes have required the use of a number of processing steps which often increased the cost of making the final product.

We have now discovered, unexpectedly that we are able to make the precursor tetracarboxylic acid of formula I by effecting reaction between a 4-nitro-N-alkylphthalimide of formula II with an aromatic dihydroxy compound of formula III employing a specific set of conditions, namely, the use of a specific catalyst, potassium carbonate, and a specific solvent, dimethylsulfoxide. It was entirely unexpected and in no way could have been predicted that this set of conditions could lead to a process which would give the desired results. For instance, when sodium carbonate was employed instead of potassium carbonate, it was found that the reaction did not proceed anywhere near the rate or yield of product as occurred when potassium carbonate was employed. In addition, when other solvents, both aprotic and non-aprotic, were used in place of dimethylsulfoxide, such as methanol, methylene chloride, acetone, dimethylformamide, etc., it was found that little, if any, reaction occurred. It was only when one employed this particular combination of ingredients, namely, the potassium carbonate and the dimethylsulfoxide solvent with the above-mentioned reactants of formula II and formula III that one was able to obtain good yields of the tetracarboxylic acid. The tetracarboxylic acid could then be readily dehydrated to form the dianhydride of formula IV.

Among the 4-nitro-N-alkylphthalimides which may be employed are, for instance, 4-nitro-N-methylphthalimide and 4-nitro-N-ethylphthalimide.

In addition to the aromatic dihydroxy compounds which are obvious from a reading of formula III, other dihydric phenols which may be employed are, for instance, 2,2-bis-(2-hydroxyphenyl)propane;
2,4'-dihydroxydiphenylmethane;
bis-(2-hydroxyphenyl)-methane;
2,2-bis-(4-hydroxyphenyl)-propane (hereinafter identified as "bisphenol-A" or "BPA")
1,1-bis-(4-hydroxyphenyl)-ethane;
1,1-bis-(4-hydroxyphenyl)-propane;
2,2-bis-(4-hydroxyphenyl)-pentane;
3,3-bis-(4-hydroxyphenyl)-pentane;
4,4'-dihydroxybiphenyl;
4,4'-dihydroxy-3,3',5,5'-tetramethylbiphenyl;
2,4-dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide; etc.

In carrying out the reaction, one should employ at least 2 mols of the alkylphthalimide of formula II and preferably from 2.1 to 4 or more mols of the latter per mol of the aromatic dihydroxy compound of formula III. Obviously, too large a molar excess will present problems of separation and recovery of the unused alkylphthalimide.

The amount of potassium carbonate employed can be varied widely. Generally, we have found that at least two mols of the potassium carbonate should be employed per mol of the dihydric phenol and preferably from about 2.1 to 3 or 4 mols of the former per mol of the dihydric phenol are advantageously used.

The amount of dimethylsulfoxide can also be varied widely but enough of the latter solvent should be used in order to form a liquid medium for effecting the reaction. On a weight basis, we have found it convenient to use from about 1 to 20 parts or more, by weight, of the dimethylsulfoxide, per weight unit of the total weight of the two reactants, namely, the alkylphthalimide and the dihydric phenol.

In all instances, substantially anhydrous conditions should be employed and for best results, an inert atmosphere should be employed, such as conducting the reaction under a blanket of nitrogen. The temperature at which the reaction is carried out can be varied widely and should be in excess of 100° C., for example, from about 110° to 200° C. or possibly higher depending upon the reactants employed, the concentration of the various materials used in conducting the reaction, etc. The reaction should be carried out for a sufficient time to insure that complete interreaction of the reactants has occurred. This will generally take anywhere from about 30 minutes to 48 hours or more. Stirring should be resorted to at all times in order to insure intimate contact of all the reactants and reagents required for optimum processing. After the reaction is carried out, treatment with a base and then with an acid such as hydrochloric acid, sulfuric acid, etc., will convert the reaction product to a tetracarboxylic acid derivative of formula I.

Our process offers several advantages over previous methods for making the tetraacid from the reaction of a dihydric phenol and a nitro-N-alkylphthalimide employing an alkali metal hydroxide in the form of the dianion of the dihydric phenol. In the past, the salt formed from the reaction of the dihydric phenol and the alkali metal hydroxide had to be kept under an inert atmosphere to avoid rapid air-oxidation and had to be completely anhydrous before it could be allowed to undergo the aromatic nitro-displacement reaction to form the precursor N-alkyl phthalimide compound. In addition, water had to be removed from the salt thus formed and this required a long period of time, for instance, from two to four days using a complex step of azeotropic distillation with toluene. Even after most of the water had been removed, it was necessary to scavenge the remaining amounts of water with dehydrating agents, such as calcium hydride, which could be somewhat toxic and expensive. Furthermore, once the dianion salt had been isolated, two equivalents of the alkylphthalimide were added and the displacement reaction was then allowed to proceed for another period of time ranging from about 6 to 24 hours with ultimate workup required of the reaction product to isolate the desired bis-imide which, in a subsequent step, could then be converted to the corresponding tetraacid.

Our nitro-displacement reaction is significantly simplified because we are able to generate substituted-phenoxide ions in situ with an inorganic base in the presence of the nitrophthalimide, thus avoiding the need to prepare the dianion of the dihydric phenol in advance. Although it was expected that imide-ring opening by potassium carbonate would compete with the nitro-displacement reaction, it was surprising to find that the ring opened compound was not deactivated enough to prevent a nitro-displacement. Also it was found that the dihydric phenol was converted to components which were free of phenol end-groups and instead had end-groups which could readily proceed to the di-carboxy state. In fact, even though the reaction between the alkylphthalimide and the dihydric phenol in the presence of potassium carbonate and dimethylsulfoxide as the solvent led to a mixture of compounds which can be represented by the formula

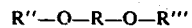  V where R has the meaning above, and R" and R"' are independently selected from the groups listed in Table of End Groups Below,

TABLE OF END GROUPS

| R" and R'" Formulas | Designation |
|---|---|
| 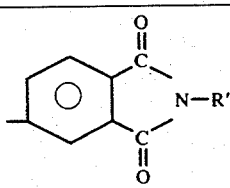 | "Imide" |
| 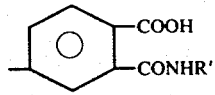 | "1-Acid" |
| 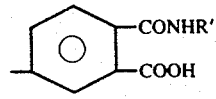 | "2-Acid" |
| 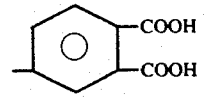 | "Diacid" |
| 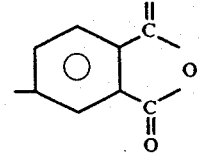 | "Anhydride" | these compounds could be readily converted to the tetracarboxylic acid derivative of formula I by base hydrolysis and subsequent acidification with a mineral acid. This enabled one to be unconcerned with what was present in the reaction mixture after interacting the alkylphthalimide with the dihydric phenol.

In order that those skilled in the art may better understand how the present invention may be practiced, the following examples are given by way of illustration and not by way of limitation.

EXAMPLE 1

A mixture of 9.06 grams (0.044 mol) of 4-nitro-N-methylphthalimide, 4.56 grams (0.02 mol) of BPA, 6.90 grams (0.05 mol) of potassium carbonate ($K_2CO_3$), and 30 ml of dimethylsulfoxide were heated under a nitrogen atmosphere for 4 hours at a temperature of about 165° C. After cooling to about 25° C., the mixture was added to an excess amount of aqueous HCl sufficient to neutralize the potassium ions present in the mixture. The precipitated solid which was obtained was filtered, and air-dried to give a yield of 11.60 grams of a mixture of ingredients V, wherein the percents of end-groups, R" and R'", were determined approximately by $^{13}C$—NMR ("end-group" as identified previously and percent given): imide, 29%; 1-acid, 19%; 2-acid, 33%; diacid, 16%; anhydride, 3%. No unreacted phenol end-groups could be detected. Using 10.6 grams of the aforesaid mixture of end-terminated compounds, 10.6 grams of 50% aqueous sodium hydroxide and 21 ml water were stirred in with the mixture and heated at the reflux temperature of the mass (about 104° C.) for approximately 24 hours. The reaction mixture was worked up with excess aqueous HCl including heating the mixture to induce the product to crystallize. Filtration and drying of the reaction product yielded 8 grams of the tetra-acid of formula I in essentially, completely pure form.

EXAMPLE 2

When Example 1 was repeated with the exception that a smaller excess of 4-nitro-N-methylphthalimide (8.65 grams, 0.042 mol) was employed, the isolated yield of the mixture containing the various end groups was 11.80 grams and its $^{13}C$-NMR end-group approximate analysis was: imide, 24%; 1-acid, 15%; 2-acid, 33%; diacid, 23%; anhydride, 5%. Again, no unreacted phenol end-groups were detected.

EXAMPLE 3

2.82 Grams of 4-nitro-N-methylphthalimide, 1.73 grams of potassium carbonate, and 1.09 grams of 4,4'-dihydroxydiphenyl sulfide were stirred with 10 ml of dimethylsulfoxide and heated at 162° C. for about 4 hours. On cooling the reaction mass to room temperature, 10 ml water was added and the product was isolated by adding the reaction mixture to 100 ml of 3N HCl. The resultant pasty solid was separated from the aqueous solution, dried in a vacuum oven and then analyzed by $^{13}C$-NMR spectroscopy. The composition of this product mixture was analogous to that found previously in connection with Example 1, with the exception that no anhydride end-groups were observed. However, once again no unreacted phenol end-group could be detected which would interfere with the conversion to the tetra-acid derivative. This product mixture can be converted to the tetra-acid having the formula

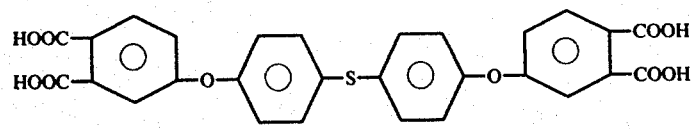

VI by treatment first with base and then with HCl similar to the procedure used to produce the tetra-acid in Example 1.

It will of course be apparent to those skilled in the art that instead of using the 4-nitro-N-methylphthalimide of the foregoing examples, the other N-alkylphthalimide, namely, 4-nitro-N-ethylphthalimide can be employed in its place without departing from the scope of the invention. In addition, instead of employing the dihydric phenols in Examples 1 to 3, other dihydric phenols, many examples which have been given above, can be used in their place within the intended scope of the invention and with equivalent results. Finally, it will be apparent that the concentrations of ingredients, the conditions of reactions can also be varied widely as previously recited to obtain the desired tetra-acid derivatives expeditiously and in almost quantitative yields.

As pointed out above, the tetra-acids obtained in accordance with the present invention may be dehydrated to form the dianhydrides which in turn can be reacted with various organic diamines such as metaphenylene diamine, 4,4'-diaminodiphenylmethane, benzidine, 4,4'-diaminodiphenylsulfone, 3,3'-dimethylbenzidine, etc., to yield resinous compositions which because of their desirable heat resistance can be employed in applications where elevated temperatures may be encountered. Thus, these polymeric compositions, whether filled or unfilled, can be employed in applications requiring good mechanical, electrical and heat resistance properties. They are eminently suitable for use in the manufacture of insulators, transformer blocks, motor armatures, printed circuits, honeycomb structure panels and compressor vanes, etc. In the form of solutions with suitable solvents, they can be used to coat electrical conductors such as copper or aluminum wire and the resinous materials so deposited can be heat-treated to effect conversion to the final polymerized state.

What we claim as new and desire to secure by Letters Patent is:

1. The process of making a tetracarboxylic acid of the formula

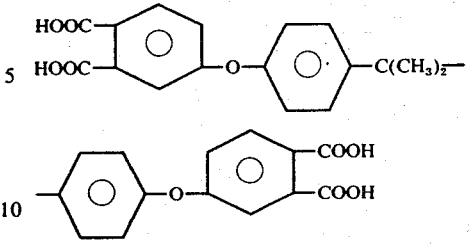

which comprises (1) simultaneously effecting reaction under substantially anhydrous conditions and in an inert atmosphere at a temperature within the range of from about 110° to 200° C between a nitrophthalimide of the formula

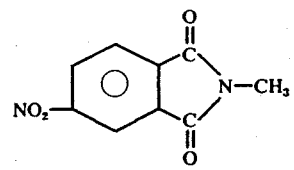

with bisphenol-A, the said reaction being conducted in a dimethyl sulfoxide solvent and in the presence of potassium carbonate in a mol ratio of from 2.1 to 3 mols of the latter per mol of bisphenol-A, and converting the resulting bisimide product by hydrolysis to the abovedescribed tetracarboxylic acid.

* * * * *